(12) United States Patent
Morin

(10) Patent No.: US 6,337,200 B1
(45) Date of Patent: Jan. 8, 2002

(54) HUMAN TELOMERASE CATALYTIC SUBUNIT VARIANTS

(75) Inventor: Gregg B. Morin, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/128,354

(22) Filed: Aug. 3, 1998

Related U.S. Application Data

(63) Continuation-in-part of application No. 09/052,864, filed on Mar. 31, 1998, now abandoned.

(51) Int. Cl.⁷ .......................... C07H 21/04; C07K 1/00; C12N 5/00; C12N 15/63; C12N 15/85

(52) U.S. Cl. ................ 435/194; 435/69.1; 435/70.1; 435/320.1; 435/325; 435/440; 435/455; 514/44; 530/350; 536/23.1; 536/23.5

(58) Field of Search ................ 536/23.5, 23.1, 536/24.5; 435/69.1, 325, 70.1, 71.1, 320.1, 440, 455; 514/44; 530/350

(56) References Cited

PUBLICATIONS

Bodnar et al., "Extension of Life–Span by Introduction of Telomerase into Normal Human Cells" *Science* 279: 349–352.

Harrington et al., 1997, "Human telomerase contains evolutionarily conserved catalytic and structural subunits-"*Genes Dev. 11:* 3109–3115.

Kilian et al., 1997, "Isolation of a candidate human telomerase catalytic subunit gene, which reveals complex splicing patterns in different cell types" *Hum. Mol. Genet. 6:* 2011–2019.

Meyerson et al., 1997, "hEST2, the Putative Human Telomerase Catalytic Subunit Gene, Is Up–Regulated in Tumor Cells and during Immortalization" *Cell 90:* 785–795.

Nakamura et al., 1997, "Telomerase Catalytic Subunit Homologs from Fission Yeast and Human" *Science 277:* 955.

Weinrich et al., 1997, "Reconstitution of human telomerase with the template RNA component hTR and the catalytic protein subunit hTRT" *Nat. Genet. 1997 Dec. 1:* 17(4):498–502.

*Primary Examiner*—Deborah Crouch
*Assistant Examiner*—Anne-Marie Baker
(74) *Attorney, Agent, or Firm*—Geron Corporation; J. Michael Schiff; David J. Earp

(57) ABSTRACT

The invention provides compositions and methods related to human telomerase reverse transcriptase (hTRT), the catalytic protein subunit of human telomerase. Catalytically active human telomerase reverse transcriptase variants comprising deletions or other mutations are provided.

11 Claims, 2 Drawing Sheets

```
MPRAPRCRAVRSLLRSHYREVLPLATFVRRLGPQGWRLVQRGDP
AAFRALVAQCLVCVPWDARPPPAAPSFRQVSCLKELVARVLQRL
CERGAKNVLAFGFALLDGARGGPPEAFTTSVRSYLPNTVTDALR
GSGAWGLLLRRVGDDVLVHLLARCALFVLVAPSCAYQVCGPPLY
QLGAATQARPPPHASGPRRRLGCERAWNHSVREAGVPLGLPAPG
ARRRGGSASRSLPLPKRPRRGAAPEPERTPVGQGSWAHPGRTRG
PSDRGFCVVSPARPAEEATSLEGALSGTRHSHPSVGRQHHAGPP
STSRPPRPWDTPCPPVYAETKHFLYSSGDKEQLRPSFLLSSLRP
SLTGARRLVETIFLGSRPWMPGTPRRLPRLPQRYWQMRPLFLEL
LGNHAQCPYGVLLKTHCPLRAAVTPAAGVCAREKPQGSVAAPEE
EDTDPRRLVQLLRQHSSPWQVYGFVRACLRRLVPPGLWGSRHNE
RRFLRNTKKFISLGKHAKLSLQELTWKMSVRDCAWLRRSPGVGC
VPAAEHRLREEILAKFLHWLMSVYVVELLRSFFYVTETTFQKNR
LFFYRKSVWSKLQSIGIRQHLKRVQLRELSEAEVRQHREARPAL
LTSRLRFIPKPDGLRPIVNMDYVVGARTFRREKRAERLTSRVKA
LFSVLNYERARRPGLLGASVLGLDDIHRAWRTFVLRVRAQDPPP
ELYFVKVDVTGAYDTIPQDRLTEVIASIIKPQNTYCVRRYAVVQ
KAAHGHVRKAFKSHVSTLTDLQPYMRQFVAHLQETSPLRDAVVI
EQSSSLNEASSGLFDVFLRFMCHHAVRIRGKSYVQCQGIPQGSI
LSTLLCSLCYGDMENKLFAGIRRDGLLLRLVDDFLLVTPHLTHA
KTFLRTLVRGVPEYGCVVNLRKTVVNFPVEDEALGGTAFVQMPA
HGLFPWCGLLLDTRTLEVQSDYSSYARTSIRASLTFNRGFKAGR
NMRRKLFGVLRLKCHSLFLDLQVNSLQTVCTNIYKILLLQAYRF
HACVLQLPFHQQVWKNPTFFLRVISDTASLCYSILKAKNAGMSL
GAKGAAGPLPSEAVQWLCHQAFLLKLTRHRVTYVPLLGSLRTAQ
TQLSRKLPGTTLTALEAAANPALPSDFKTILD
```

FIG. 1

```
   1 gcagcgctgc gtcctgctgc gcacgtggga agccctggcc ccggccaccc ccgcgatgcc
  61 gcgcgctccc cgctgccgag ccgtgcgctc cctgctgcgc agccactacc gcgaggtgct
 121 gccgctggcc acgttcgtgc ggcgcctggg gccccagggc tggcggctgg tgcagcgcgg
 181 ggacccggcg gctttccgcg cgctggtggc ccagtgcctg gtgtgcgtgc cctgggacgc
 241 acggccgccc ccgccgccc cctccttccg ccaggtgtcc tgcctgaagg agctggtggc
 301 ccgagtgctg cagaggctgt gcgagcgcgg cgcgaagaac gtgctggcct cggcttcgc
 361 gctgctggac ggggcccgcg ggggccccc cgaggccttc accaccagcg tgcgcagcta
 421 cctgcccaac acggtgaccg acgcactgcg ggggagcggg gcgtgggggc tgctgctgcg
 481 ccgcgtgggc gacgacgtgc tggttcacct gctggcacgc tgcgcgctct ttgtgctggt
 541 ggctcccagc tgcgcctacc aggtgtgcgg gccgccgctg taccagctcg gcgctgccac
 601 tcaggcccgg cccccgccac acgctagtgg accccgaagg cgtctgggat gcgaacgggc
 661 ctggaaccat agcgtcaggg aggccggggt cccctgggc ctgccagccc cgggtgcgag
 721 gaggcgcggg ggcagtgcca gccgaagtct gccgttgccc aagaggccca ggcgtggcgc
 781 tgcccctgag ccggagcgga cgcccgttgg gcaggggtcc tgggcccacc cgggcaggac
 841 gcgtggaccg agtgaccgtg gtttctgtgt ggtgtcacct gccagacccg ccgaagaagc
 901 cacctctttg gagggtgcgc tctctggcac gcgccactcc caccatccg tgggccgcca
 961 gcaccacgcg ggcccccat ccacatcgcg gccaccacgt ccctgggaca cgccttgtcc
1021 cccggtgtac gccgagacca agcacttcct ctactcctca ggcgacaagg agcagctgcg
1081 gccctccttc ctactcagct ctctgaggcc cagcctgact ggcgctcgga ggctcgtgga
1141 gaccatcttt ctgggttcca ggccctggat gccagggact ccccgcaggt tgccccgcct
1201 gccccagcgc tactggcaaa tgcggcccct gtttctggag ctgcttggga accacgcgca
1261 gtgccctac ggggtgctcc tcaagacgca ctgcccgctg cgagctgcgg tcacccagc
1321 agccggtgtc tgtgcccggg agaagcccca gggctctgtg gcggccccg aggaggagga
1381 cacagacccc cgtcgcctgg tgcagctgct ccgccagcac agcagccct ggcaggtgta
1441 cggcttcgtg cgggcctgcc tgcgccggct ggtgccccca ggcctctggg gctccaggca
1501 caacgaacgc cgcttcctca ggaacaccaa gaagttcatc tccctgggga agcatgccaa
1561 gctctcgctg caggagctga cgtggaagat gagcgtgcgg gactgcgctt ggctgcgcag
1621 gagcccaggg gttggctgtg ttccggccgc agagcaccgt ctgcgtgagg agatcctggc
1681 caagttcctg cactggctga tgagtgtgta cgtcgtcgag ctgctcaggt cttcttta
1741 tgtcacggag accacgtttc aaaagaacag gctcttttc taccggaaga gtgtctggag
1801 caagttgcaa agcattggaa tcagacagca cttgaagagg gtgcagctgg gggagctgtc
1861 ggaagcagag gtcaggcagc atcgggaagc caggcccgcc ctgctgacgt ccagactccg
1921 cttcatcccc aagcctgacg ggctgcggcc gattgtgaac atggactacg tcgtgggagc
1981 cagaacgttc cgcagagaaa agagggccga gcgtctcacc tcgagggtga aggcactgtt
2041 cagcgtgctc aactacgagc gggcgcggcg ccccggcctc ctgggcgcct ctgtgctggg
2101 cctggacgat atccacaggg cctggcgcac cttcgtgctg cgtgtgcggg cccaggaccc
2161 gccgcctgag ctgtactttg tcaaggtgga tgtgacgggc gcgtacgaca ccatccccca
2221 ggacaggctc acggaggtca tcgccagcat catcaaaccc cagaacacgt actgcgtgcg
2281 tcggtatgcc gtggtccaga aggccgccca tgggcacgtc cgcaaggcct tcaagagcca
2341 cgtctctacc ttgacagacc tccagccgta catgcgacag ttcgtggctc acctgcagga
2401 gaccagcccg ctgagggatg ccgtcgtcat cgagcagagc tcctccctga tgaggccag
2461 cagtggcctc ttcgacgtct tcctacgctt catgtgccac cacgccgtgc gcatcagggg
2521 caagtcctac gtccagtgcc agggatccc gcagggctcc atcctctcca cgctgctctg
2581 cagcctgtgc tacggcgaca tggagaacaa gctgtttgcg gggattcggc gggacgggct
2641 gctcctgcgt ttggtggatg atttcttgtt ggtgacacct cacctcaccc acgcgaaaac
2701 cttcctcagg accctggtcc gaggtgtccc tgagtatggc tgcgtggtga acttgcggaa
2761 gacagtggtg aacttccctg tagaagacga ggccctgggt ggcacggctt ttgttcagat
2821 gccggcccac ggcctattcc cctggtgcgg cctgctgctg gatacccgga ccctggaggt
2881 gcagagcgac tactccagct atgcccggac ctccatcaga gccagtctca ccttcaaccg
2941 cggcttcaag gctgggagga acatgcgtcg caaactcttt ggggtcttgc ggctgaagtg
3001 tcacagcctg tttctggatt tgcaggtgaa cagcctccag acggtgtgca ccaacatcta
3061 caagatcctc ctgctgcagg cgtacaggtt tcacgcatgt gtgctgcagc tcccatttca
3121 tcagcaagtt tggaagaacc ccacattttc cctgcgcgtc atctctgaca cggcctccct
3181 ctgctactcc atcctgaaag ccaagaacgc agggatgtcg ctggggggcca agggcgccgc
3241 cggccctctg ccctccgagg ccgtgcagtg gctgtgccac caagcattcc tgctcaagct
3301 gactcgacac cgtgtcacct acgtgccact cctggggtca ctcaggacag cccagacgca
3361 gctgagtcgg aagctcccgg ggacgacgct gactgccctg gaggccgcag ccaacccggc
3421 actgccctca gacttcaaga ccatcctgga ctgatggcca cccgcccaca gccaggccga
3481 gagcagacac cagcagccct gtcacgccgg gctctacgtc ccagggaggg agggcggcc
3541 cacacccagg cccgcaccgc tgggagtctg aggcctgagt gagtgtttgg ccgaggcctg
3601 catgtccggc tgaaggctga gtgtccggct gaggcctgag cgagtgtcca gccaagggct
3661 gagtgtccag cacacctgcc gtcttcactt ccccacaggc tggcgctcgg ctccaccca
3721 gggccagctt ttcctcacca ggagcccggc ttccactccc cacataggaa tagtccatcc
3781 ccagattcgc cattgttcac ccctcgccct gccctccttt gccttccacc cccaccatcc
3841 aggtggagac cctgagaagg accctgggag ctctgggaat ttggagtgac caaaggtgtg
3901 ccctgtacac aggcgaggac cctgcacctg gatggggtc cctgtgggtc aaattggggg
3961 gaggtgctgt gggagtaaaa tactgaatat atgagttttt cagttttgaa aaaaa
```

FIG. 2

HUMAN TELOMERASE CATALYTIC SUBUNIT VARIANTS

CROSS-REFERENCE TO RELATED APPLICATIONS

This application is a continuation-in-part of U.S. patent application Ser. No. 09/052,864, filed Mar. 31, 1998, now abandoned.

The priority application is hereby incorporated herein by reference in its entirety, as are the following: U.S. application Ser. No. 08/851,843, filed May 6, 1997, now U.S. Pat. No. 6,093,809; Ser. No. 08/854,050, filed May 9, 1997, now U.S. Pat. No. 6,261,836; Ser. No. 08/911,312, filed Aug. 14, 1997, still pending; Ser. No. 08/912,951, filed Aug. 14, 1997, still pending; Ser. No. 08/915,503, filed Aug. 14, 1997, now abandoned; Ser. No. 08/974,549, filed Nov. 19, 1997, now U.S. Pat. No. 6,166,178; and Ser. No. 08/974,584, filed Nov. 18, 1997, still pending; and International Applications PCT/US97/17618 and PCT/US97/17885, which designate the U.S.

FIELD OF THE INVENTION

The present invention is related to the catalytic protein subunit of human telomerase. The invention provides methods and compositions relating to medicine, molecular biology, chemistry, pharmacology, and medical diagnostic and prognostic technology.

BACKGROUND OF THE INVENTION

The following discussion is intended to introduce the field of the present invention to the reader. The citation of various references in this section should not be construed as an admission of prior invention.

It has long been recognized that complete replication of the ends of eukaryotic chromosomes requires specialized cell components (Watson, 1972, *Nature New Biol.*, 239:197; Olovnikov, 1973, *J. Theor. Biol.*, 41:181). Replication of a linear DNA strand by conventional DNA polymerase requires an RNA primer, and can proceed only 5' to 3'. When the RNA bound at the extreme 5' ends of eukaryotic chromosomal DNA strands is removed, a gap is introduced, leading to a progressive shortening of daughter strands with each round of replication. This shortening of telomeres, the protein-DNA structures physically located on the ends of chromosomes, is thought to account for the phenomenon of cellular senescence or aging of normal human somatic cells in vitro and in vivo. The maintenance of telomeres is a function of a telomere-specific DNA polymerase known as telomerase. Telomerase is a ribonucleoprotein (RNP) that uses a portion of its RNA moiety as a template for telomeric DNA synthesis (Morin, 1997, *Eur. J. Cancer* 33:750). The length and integrity of telomeres and the telomerase expression status of a cell is thus related to entry of a cell into a senescent stage (i.e., loss of proliferative capacity), or the ability of a cell to escape senescence, i.e., to become immortal.

Consistent with the relationship of telomeres and telomerase to the proliferative capacity of a cell (i.e., the ability of the cell to divide indefinitely), telomerase activity is detected in immortal cell lines and an extraordinarily diverse set of tumor tissues, but is not detected (i.e., was absent or below the assay threshold) in normal somatic cell cultures or normal tissues adjacent to a tumor (see, U.S. Pat. Nos. 5,629,154; 5,489,508; 5,648,215; and 5,639,613; see also, Morin, 1989, *Cell* 59: 521; Shay and Bacchetti 1997, *Eur. J. Cancer* 33:787; Kim et al., 1994, *Science* 266:2011; Counter et al., 1992, *EMBO J.* 11:1921; Counter et al., 1994, *Proc. Natl. Acad. Sci. U.S.A.* 91, 2900; Counter et al., 1994, *J. Virol.* 68:3410). Moreover, a correlation between the level of telomerase activity in a tumor and the likely clinical outcome of the patient has been reported (e.g., U.S. Pat. No. 5,639,613, supra; Langford et al., 1997, *Hum. Pathol.* 28:416). Thus, human telomerase is an ideal target for diagnosing and treating human diseases relating to cellular proliferation and senescence, such as cancer, or for increasing the proliferative capacity of a cell.

BRIEF SUMMARY OF THE INVENTION

In one aspect, the invention provides an isolated or recombinant hTRT polypeptide that has telomerase catalytic activity. In one embodiment, the hTRT polypeptide has a deletion of at least 25 residues in the regions corresponding to residues 192–323, 200–323, 192–271, 200–271, 222–240, 415–450, 192–323 and 415–450, or 192–271 and 415–450 of hTRT. In a related embodiment, residues 192–323, 200–323, 192–271, 200–271, 222–240, 415–450, 192–323 and 415–450, or 192–271 and 415–450 of hTRT are deleted. The invention also provides a polynucleotide comprising a nucleotide sequence encoding these hTRT polypeptides. In some embodiments, the polynucleotide includes a promoter sequence operably linked to the nucleotide sequence encoding the hTRT polypeptide.

The invention also provides a method of preparing recombinant telomerase by contacting a recombinant hTRT polypeptide containing a deletion as described supra with a telomerase RNA component under conditions such that the recombinant protein and the telomerase RNA component associate to form a telomerase enzyme capable of catalyzing the addition of nucleotides to a telomerase substrate. The hTRT polypeptide may be produced in an in vitro expression system and/or may be purified before the contacting step. In some embodiments, the contacting occurs in a cell.

The invention further provides a method for increasing the proliferative capacity of a vertebrate cell by introducing into a cell the recombinant hTRT polynucleotide encoding an hTRT deletion variant described supra. In a related embodiment, the invention provides a cell, such as a human cell or other mammalian cell, comprising a nucleotide sequence that encodes the hTRT deletion variant polypeptide. The invention provides such cells that have an increased proliferative capacity relative to a cell that is otherwise identical but does not comprise the recombinant polynucleotide.

In a different aspect of the invention, an isolated or recombinant hTRT polypeptide that has a deletion of amino acid residues 192–450, 560–565, 637–660, 638–660, 748–766, 748–764, or 1055–1071, where the residue numbering is with reference to the hTRT polypeptide having the sequence provided in FIG. 1, is provided. In a related aspect, the invention provides an isolated, recombinant, or substantially purified polynucleotide encoding this polypeptide, which in some embodiments includes a promoter sequence operably linked to the nucleotide sequence encoding the hTRT polypeptide.

The invention also provides a method of reducing telomerase activity in a cell by introducing the polynucleotide described supra (i.e., having a deletion of deletion of amino acid residues 192–450, 560–565, 637–660, 638–660, 748–766, 748–764, or 1055–1071) into a cell under conditions in which it is expressed.

In a related embodiment, the hTRT polypeptide has one or more mutations other than, or in addition to, a deletion of at least 25 residues in the regions corresponding to residues 192–323, 200–323, 192–271, 200–271, 222–240, 415–450, 192–323 and 415–450, or 192–271 and 415–450 of hTRT.

DESCRIPTION OF THE FIGURES

FIG. 1 shows the amino acid sequence of a 1132-residue human telomerase reverse transcriptase (hTRT) protein (SEQ ID NO:2).

FIG. 2 shows the nucleotide sequence of a naturally occurring cDNA encoding the hTRT protein (SEQ ID NO:1).

DETAILED DESCRIPTION OF THE INVENTION

I. Introduction

Telomerase is a ribonucleoprotein complex (RNP) comprising an RNA component and a catalytic protein component. The catalytic protein component of human telomerase, hereinafter referred to as telomerase reverse transcriptase ("hTRT"), has been cloned, and protein, cDNA and genomic sequences determined. See, e.g., Nakamura et al., 1997, *Science* 277:955, and copending U.S. patent application Ser. No. 08/912,951 filed Aug. 14, 1997, still pending and Ser. No. 08/974,549, filed Nov. 19, 1997, now U.S. Pat. No. 6,166,178. The sequence of a full-length native hTRT has been deposited in GenBank (Accession No. AF015950), and plasmid and phage vectors having hTRT coding sequences have been deposited with the American Type Culture Collection, Rockville, Md. (accession numbers 209024, 209016, and 98505). The catalytic subunit protein of human telomerase has also been referred to as "hEST2" (Meyerson et al., 1997, *Cell* 90:785), "hTCS1" (Kilian et al., 1997, *Hum. Mol. Genet.* 6:2011), "TP2" (Harrington et al., 1997, *Genes Dev.* 11:3109), and "hTERT" (e.g., Greider, 1998, *Curr. Biol.* 8:R178–R181). Human TRT is also described in the aforereferenced priority applications and U.S. patent application Ser. No. 08/846,017, now abandoned, Ser. No. 08/844,419, now abandoned, and Ser. No. 08/724,643,now abandoned. The RNA component of human telomerase (hTR) has also been characterized (see U.S. Pat. No. 5,583,016). All of the aforementioned applications and publications are incorporated by reference herein in their entirety and for all purposes.

Human TRT is of extraordinary interest and value because, inter alia, telomerase activity in human cells and other mammalian cells correlates with cell proliferative capacity, cell immortality, and the development of a neoplastic phenotype. Thus, hTRT polypeptides, including the hTRT variants described herein, and polynucleotides encoding hTRT polypeptides, are used, inter alia for conferring a telomerase activity (e.g., telomerase catalytic activity, infra) in a telomerase-negative cell such as a cell from a human, a mammal, a vertebrate, or other eukaryote (see, e.g., Bodnar et al., 1998, *Science* 279:349 and copending U.S. patent application Ser. No. 08/912,951, still pending and Ser. No. 08/974,549, now U.S. Pat. No. 6,166,178). Variants that lack at least one hTRT activity (e.g., telomerase catalytic activity) are used, inter alia, to inhibit telomerase activity in a cell (e.g., by acting as "dominant negative mutants"). The hTRT variants and polynucleotides encoding them, as described herein, are similarly useful in screening assays for identifying agents that modulate telomerase activity.

The hTRT variants of the present invention are characterized by one or more deletions or mutations, relative to a naturally occurring hTRT polypeptide, in defined regions of the protein, as described in detail infra. These hTRT variants may have none, one, or several of the biological activities that may be found in naturally-occurring full-length hTRT proteins. These activities include telomerase catalytic activity (the ability to extend a DNA primer that functions as a telomerase substrate by adding a partial, one, or more than one repeat of a sequence, e.g., TTAGGG, encoded by a template nucleic acid, e.g., hTR), telomerase conventional reverse transcriptase activity (see Morin, 1997, supra, and Spence et al., 1995, *Science* 267:988); nucleolytic activity (see Morin, 1997, supra; Collins and Grieder, 1993, *Genes and Development* 7:1364; Joyce and Steitz, 1987, *Trends Biochem. Sci.* 12:288); primer (telomere) binding activity (see, Morin, 1997, supra; Collins et al., 1995, *Cell* 81:677; Harrington et al., 1995, *J. Biol. Chem.* 270:8893); dNTP binding activity (Morin, 1997, supra; Spence et al., supra); and RNA (e.g., hTRT) binding activity (see Morin, 1997, supra; Harrington et al., 1997, *Science* 275:973; Collins et al., 1995, *Cell* 81:677).

In one embodiment of the invention, the hTRT variant has telomerase catalytic activity. Telomerase catalytic activity may be processive or nonprocessive. Processive telomerase catalytic activity occurs when a telomerase RNP adds multiple repeats to a primer or telomerase before the DNA is released by the enzyme complex (see, e.g., Morin, 1989, *Cell* 59:521 and Morin, 1997, *Eur. J. Cancer* 33:750). Nonprocessive activity occurs when telomerase adds a partial, or only one, repeat to a primer and is then released (see Morin, 1997, supra). In a particular embodiment of the invention, the hTRT variant has processive telomerase catalytic activity.

Processive telomerase catalytic activity can be assayed by a variety of methods, including the "conventional assay" (Morin, 1989, *Cell* 59:521), the TRAP assay (U.S. Pat. No. 5,629,154; see also, PCT publication WO 97/15687, PCT publication WO 95/13381; Krupp et al. *Nucleic Acids Res.*, 1997, 25: 919; Wright et al., 1995, *Nuc. Acids Res.* 23:3794), the "dot blot immunoassay" (U.S. patent application Ser. No. 08/833,377 now U.S. Pat. No. 5,968,506), and other assays (e.g., Tatematsu et al., 1996, *Oncogene* 13:2265). The TRAPeze™ Kit (Oncor, Inc., Gaithersburg, Md.) may be used. The telomerase substrate used in these assays may have a natural telomere sequence, or may be have a synthetic oligonucleotide with a different sequence (see, e.g., Morin, 1989, *Cell* 59:521; Morin, 1991, *Nature* 353:454–56).

As used herein, an hTRT variant is considered to have a specified activity if the activity is exhibited by either the hTRT variant polypeptide without an associated hTR RNA or in an hTRT-hTR complex. Each of the hTRT activities described supra is also described in detail in copending U.S. patent applications Ser. No. 08/912,951 still pending and 08/974,549, now U.S. Pat. No. 6,166,178.

II. hTRT Variants Described a) hTRT Variants with Telomerase Catalytic Activity

It has now been demonstrated that large regions of the hTRT protein can be mutated (e.g., deleted) without loss of telomerase catalytic activity. Sites of mutation (e.g., deletion) are described herein with reference to the amino acid sequence provided in FIG. 1 and encoded in plasmid pGRN121 (ATCC accession number 209016); however it will be recognized that the same or equivalent mutations may be made in other hTRT polypeptides, e.g., naturally occurring variants such as polymorphic variants, hTRT fusion proteins, hTRT homologs (e.g., from non-human species), and the like. For ease of discussion, the residues of the full-length hTRT protein having a sequence as provided in FIG. 1 are referred to herein by number, with the amino-terminal methionine (M) in FIG. 1 numbered "1", and the carboxy-terminal aspartic acid (D) numbered "1132".

Regions of the hTRT protein that can be mutated (e.g., deleted) without abolishing telomerase catalytic activity include the regions from amino acid residues 192 to 323 (inclusive) and residues 415 to 450 (inclusive). As is demonstrated in the experiments described infra, all or part of either of these regions, or all or part of both of them, can be deleted without abolishing the telomerase catalytic activity of the protein. The regions from amino acid residues 192 to 323 and residues 415 to 450 may be referred to as "nonessential" regions of hTRT (i.e., not essential for telomerase catalytic activity). Thus, in various embodiments, the hTRT variants of the invention comprise deletions of, or other mutations in, these nonessential regions of hTRT. As described in Section IV, infra, certain mutations (e.g., deletion of residues 415–450) alter RNA-binding characteristics of the hTRT variant.

Examples of mutations that can be made in the hTRT polypeptides of the invention include deletions, insertions, substitutions, and combination of mutations. Thus, in some embodiments the mutation is a deletion of at least one, typically at least about 10, and often at least about 25, at least about 50, or at least about 100 amino acid residues relative to a naturally occurring hTRT. In alternative embodiments, the mutation is a single amino acid substitution in a "nonessential" region, or a combinations of substitutions. Substitutions may be conservative substitutions or non-conservative substitutions. In still other embodiments, the mutation is an insertion or substitution of amino acids, for example the insertion of residues that encode an epitope tag or novel proteolytic site. Substitutions may be of one or more (e.g., all) of the residues in the above-mentioned regions or may be combined with deletions so that, e.g., a shorter heterologous sequence is a substituted for a longer hTRT sequence. It will be appreciated, as noted supra, that in some embodiments the hTRT variant has more than one different type of mutation relative to a naturally occurring hTRT protein (e.g., a deletion and a point mutation).

The hTRT variants of the invention have certain advantages compared to naturally occurring hTRT proteins. In some embodiments, mutations may confer more efficient in vitro expression of active hTRT (e.g., in expression systems in which shorter polypeptides are more efficiently expressed than longer polypeptides), may provide sequences that aid in purification (e.g., an epitope tag sequence), or may add a new functional moiety to the hTRT polypeptide (e.g., a 3'→5' exonuclease domain from DNA polymerase I).

As noted supra, the hTRT variant polypeptides of the invention comprising mutations (e.g., deletions) in the "nonessential" regions of the hTRT retain telomerase catalytic activity. These variants, and polynucleotides that encode them, are useful in any application for which other catalytically active hTRT proteins (e.g., wild-type hTRT proteins) or polynucleotides may be used, including, inter alia, in therapeutic, diagnostic, and screening uses. Exemplary uses of hTRT polypeptides and polynucleotides are described in additional detail in the afore cited copending applications (e.g., U.S. Ser. No. 08/912,951, still pending and Ser. No. 08/974,549,now U.S. Pat. No. 6,166,178).

In one embodiment, the hTRT variant of the invention is used to increase the proliferative capacity of a cell by, e.g., increasing telomerase activity in the cell (see, Bodnar et al. supra, and copending U.S. patent application Ser. No. 08/912,951, still pending and Ser. No. 08/974,549, now U.S. Pat. No. 6,166,178 for a detailed description of exemplary methods). Briefly, in one embodiment, a polynucleotide comprising (i) a sequence encoding the hTRT variant polypeptide; (ii) an operably linked promoter (e.g., a heterologous promoter); and, (iii) optionally polyadenylation and termination signals, enhancers, or other regulatory elements, is introduced into a target cell (e.g., by transfection, lipofection, electroporation, or any other suitable method) under conditions in which the hTRT variant polypeptide is expressed. The expression in the cell of the catalytically active hTRT variant of the invention results in increased proliferative capacity (e.g., an immortal phenotype).

In another embodiment, the hTRT variant is used for in vitro reconstitution (IVR) of a telomerase ribonucleoprotein (e.g., comprising the hTRT variant polypeptide and a template RNA, e.g., hTR) that has telomerase catalytic activity. In vitro reconstitution methods are described in, e.g., Weinrich et al., 1997, *Nat. Genet.* 17:498, and copending U.S. patent application Ser. No. 08/912,951, still pending and Ser. No. 08/974,549, now U.S. Pat. No. 6,166,178. Briefly, in one embodiment, an expression vector encoding an hTRT variant of the invention is expressed in an in vitro expression system (e.g., a coupled transcription-translation reticulocyte lysate system such as that described in U.S. Pat. No. 5,324,637). In a particular embodiment, the hTRT variant polypeptide is coexpressed with hTR. In an alternative embodiment, the hTRT variant and hTR are separately expressed and then combined (mixed) in vitro. In the latter method, the hTR RNA and/or hTRT polypeptide may be purified before mixing. In this context, the hTRT polypeptide is "purified" when it is separated from at least one other component of the in vitro expression system, and it may be purified to homogeneity as determined by standard methods (e.g., SDS-PAGE). The in vitro reconstituted (IVR) telomerase has a variety of uses; in particular it is useful for identifying agents that modulate hTRT activity (e.g., drug screening assays).

(b) Deletion Variants Lacking Telomerase Catalytic Activity

In an other aspect, the invention provides hTRT deletion variants that lack telomerase catalytic activity (i.e., having less than 1% of the wild type activity), as well as polynucleotides encoding the variants lacking telomerase catalytic activity. In particular, the invention provides variants comprising one or more of the following deletions relative to wild-type hTRT: residues 192–450, 637–660, 638–660, 748–766, 748–764, and 1055–1071. These variants are referred to herein as "PCA⁻ variants" (processive telomerase catalytic activity minus variants).

The PCA⁻ variant proteins and polynucleotides of the invention lacking telomerase catalytic activity are used in, inter alia, therapeutic, screening and other applications. For example, PCA⁻ variants are useful as dominant negative mutants for inhibition of telomerase activity in a cell. In one embodiment, a PCA⁻ variant is introduced into a cell (e.g., by transfection with a polynucleotide expression vector expressing the PCA⁻ variant), resulting in sequestration of a cell component (e.g., hTR) required for accurate telomere elongation. Thus, for example, administration of a polypeptide that binds hTR, a DNA primer, a telomerase-associated protein, or other cell component, but which does not have telomerase catalytic activity, is used to reduce endogenous telomerase activity in the cell or to otherwise interfere with telomere extension (e.g., by displacing active telomerase from telomeric DNA). Similarly, in certain embodiments, a PCA⁻ variant of the invention having one or several hTRT activities (i.e., other than processive telomerase catalytic activity) is used for screening for agents that specifically modulate (inhibit or activate) a telomerase activity other than telomerase catalytic activity. The use of hTRT variants as dominant negative mutants, and in other applications, is described in detail in copending U.S. patent application Ser.

No. 08/912,951, still pending and Ser. No. 08/974,549, now U.S. Pat. No. 6,166,178.

III. Making hTRT Variants

The hTRT variant polypeptides and polynucleotides of the invention may be produced using any of a variety of techniques known in the art. In one embodiment, a polypeptide having the desired sequence, or a polynucleotide encoding the polypeptide, is chemically synthesized (see, e.g., Roberge, et al., 1995, Science 269:202; Brown et al., 1979, Meth. Enzymol. 68:109). More often, the hTRT variant polypeptides and polynucleotides of the invention are created by manipulation of a recombinant polynucleotide encoding an hTRT polypeptide. Examples of suitable recombinant polynucleotides include pGRN121, supra, and other hTRT cDNA and genomic sequences.

Methods for cloning and manipulation of hTRT encoding nucleic acids (e.g., site-specific mutagenesis, linker scanning mutagenesis, and the like) are well known in the art and are described, for example, in Sambrook et al., 1989, Molecular Cloning: a Laboratory Manual, 2nd Ed., Vols. 1–3, Cold Spring Harbor Laboratory, and Ausubel et al., 1997, Current Protocols in Molecular Biology, Greene Publishing and Wiley-Interscience, New York. One convenient method for producing a polynucleotide encoding a desired hTRT deletion variant is by restriction digestion and subsequent ligation of a hTRT polynucleotide, to remove a region(s) of the polynucleotide encoding the amino acid residues to be deleted. If desired, restriction sites can be introduced or removed from a synthetic or naturally occurring hTRT gene to facilitate the production and detection of variants.

Typically, the recombinant polynucleotide encoding an hTRT variant of the invention is linked to appropriate regulatory elements (e.g., promoters, enhancers, polyadenylation signals, and the like) and expressed in a cell free system (see, e.g., Weinrich et al., supra), in bacteria (e.g., E. coli), in ex vivo animal cell culture (see, e.g., Bodnar et al., supra), in animals or plants (e.g., transgenic organisms or in gene therapy applications), or by any other suitable method. Suitable expression systems are well known in the art and include those described in Weinrich et al., and Bodnar et al., both supra, and in e.g., copending U.S. patent application Ser. No. 08/912,951, still pending and Ser. No. 08/974,549, now U.S. Pat. No. 6,166,178.

Additional hTRT variants of the invention may be made using "DNA shuffling" in vitro recombination technology (see, e.g., Crameri et al., 1998, Nature 391:288–291; Patten et al., 1997, Curr. Opin. Biotechnol. 8:724–733, Stemmer, 1994, Nature 370:389–391; Crameri et al., 1996, Nature Medicine, 2:1–3; Crameri et al., 1996, Nature Biotechnology 14:315–319; WO 95/22625; Stemmer, 1995, Science 270:1510; Stemmer et al., 1995, Gene, 164, 49–53; Stemmer, 1995, Bio/Technology, 13:549–553; Stemmer, 1994, Proc. Natl. Acad. Sci. USA 91:10747–10751). The specific deletion variants described supra, "wild-type hTRT" and non-human hTRT-homologs may be used in individually or various combinations as starting substrates to produce novel polypeptides with the desired activity. The activity or activities of the resulting polypeptides determined using the assays described in Section I, supra.

IV. Exemplary hTRT Variants a) Generally

Exemplary hTRT variants were created by in vitro mutagenesis of polynucleotides encoding a full-length hTRT protein using the method of Perez et al., 1994, J. Biol. Chem. 269:22485–87. The mutant polynucleotides were expressed in vitro and telomerase reconstituted by in vitro mixing of hTRT and human telomerase RNA as described in Weinrich et al., 1997, supra. Reconstitution reactions were carried out using 0.5 pmole, 20 pmole, and, in some cases, other amounts of added hTR. Telomerase processive catalytic activity was assayed using a modified TRAP assay (Weinrich et al., 1997, supra). The results are summarized in Table 1, infra.

TABLE 1

| Deletion Name | Oligo | Amino acids deleted | Activity[1] |
|---|---|---|---|
| pGRN234 | RT1 + RT2 | none (delete NcoI site) | + |
| pGRN226 | RT3A | 192–323 | + |
| RT3 | RT3 | 200–326 | + |
| pGRN237 | RT4A | 192–271 | + |
| RT4 | RT4 | 200–271 | + |
| pGRN210 | LM122-Nuc | 222–240 | + |
| pGRN235 | RT5 | 415–450 | + |
| pGRN242 | RT3A + RT5 | 192–326 + 415–450 | + |
| pGRN243 | RT4A + RT5 | 192–271 + 415–450 | + |
| pGRN240 | RT3A/5 | 192–450 | – |
| pGRN238 | RT6A | 637–660 | – |
| RT6 | RT 6 | 638–660 | – |
| pGRN239 | RT8A | 748–766 | – |
| RT8 | RT8 | 748–764 | – |
| pGRN241 | RT10 | 1055–1071 | – |
| pGRN236 | RT11 | 1084–1116 | – |
| pGRN209 | LM121-WG | 930–934 | – |
| pGRN231 |  | 560–565 | – |

[1]"+" = at least 40% activity compared to in vitro reconstitution using wild-type hTRT (e.g., encoded by pGRN125; see Weinrich et al., 1997, supra); "–" = less than 1% activity.

Certain of the hTRT variants described supra are altered in their ability to bind hTR. The variants encoded by pGRN235, pGRN242 and pGRN243 exhibited telomerase activity when 20 pmoles hTR (template RNA) was included in the reconstitution reaction, but showed a low or undetectable level of activity when 0.5 pmoles of hTR was used. The variable activity of these variants indicates that these variants have altered (e.g., decreased) hTR binding activity. Thus, the region from 415 to 450 is likely involved in RNA binding (e.g., by affecting the conformation of the protein).

This result suggests that the region immediately upstream of residue 415, corresponding to the conserved "CP" domain (Bryan et al., 1998, Proc. Nat'l. Acad. Sci. 95:8479–8484) is a region of contact between the hTRT protein and hTR (e.g., corresponding to about residues 405 to 418 as set forth in FIG. 1). This conclusion is supported by the relative lack of conservation of sequence when human and mouse TRT sequences are compared in the region corresponding to hTRT residues 415–450.

hTR binding to hTRT was also affected by mutations and deletions in the region 560–565. RNA binding was assayed by adding purified hTR to epitope tagged TRT proteins (i.e., including a FLAG sequence; Immunex Corp, Seattle Wash.). The hTR and protein were incubated under conditions under which tagged "wild-type" hTRT associates with template RNA (hTR), and the hTRT protein or hTRT-hTR complex (if present) were immunoprecipitated. The precipitated complex was assayed for the presence and amount of associated RNA. Deletion of residues 560–565 dramatically decreased the binding of hTR by hTRT, with the concurrent expected decrease in telomerase activity (see Table 1, pGRN231). Mutation of phenylalanine (F) to alanine (A) mutation at position 561 of hTRT (the "F561A" variant; see, Weinrich et al., 1997, supra) resulted in reduced binding of hTR: this variant did not effectively bind hTR in association reactions when hTR was present at 0.5 pmoles, and showed less-than wild-type binding at 20 pmoles hTR. Mutation of tyrosine at 562 to alanine similarly resulted in a loss of hTR binding activity (e.g., about a 70–80% reduction compared to the wild-type sequence). Mutation of threonine at position 564 to alanine resulted in a decrease in RNA binding by approximately 20% compared to wild-type. In contrast, mutation of residues 560 (F) and 565 (E) to alanine did not affect hTR binding. These results indicate that the region from 560–565 is involved in RNA binding, e.g., by providing residues that contact hTR.

As will be apparent to one of skill advised of these results, the telomerase reconstitution may be inhibited using peptides comprising the sequence corresponding the hTRT residues 405–418, 560–565, or fragments thereof, or peptide mimetics of such sequences. Thus, in one embodiment of the present invention, telomerase activity in a cell or an in vitro composition in which TRT protein and TR RNA are present, such as a telomerase reconstitution assay, is reduced by introducing to the cell or in vitro composition a polypeptide comprising the sequence FFYVTE (SEQ ID NO:3), a polypeptide comprising the sequence YGVLLKTHCPLRAA(SEQ ID NO:4), a polypeptide consisting essentially of FFYVTE(SEQ ID NO:3), a polypeptide consisting essentially of FYVT(SEQ ID NO:5), a polypeptide consisting essentially of YGVLLKTHCPLRAA (SEQ ID NO:4), a fragment of at least three residues of the aforementioned polypeptides, or a peptide analog or mimetic of the polypeptide of any of the aforementioned compositions.

Peptide mimetics (or peptide analogs) are well known and are commonly used in the pharmaceutical industry as non-peptide drugs with properties analogous to those of the template polypeptide (Fauchere, 1986, *Adv. Drug Res.* 15:29; Veber et al., 1985, *TINS p.*392; and Evans et al., 1987, *J. Med. Chem.* 30:1229). Generally, peptidomimetics are structurally similar to the paradigm polypeptide having the sequence from hTRT but have one or more peptide linkages optionally replaced by a linkage selected from the group consisting of: —CH2NH—, —CH2S—, —CH2—CH2—, —CH'CH— (cis and trans), —COCH2—, —CH(OH)CH2—, and —CH2SO—. Peptide mimetics may have significant advantages over polypeptide embodiments of this invention, including, for example: more economical production, greater chemical stability, enhanced pharmacological properties (half-life, absorption, potency, efficacy, etc.), altered specificity (e.g., a broad-spectrum of biological activities), reduced antigenicity, and others. In addition to modifications to the peptide backbone, synthetic or non-naturally occurring amino acids can also be used to substitute for the amino acids present in the polypeptide or in the functional moiety of fusion proteins. Synthetic or non-naturally occurring amino acids refer to amino acids which do not naturally occur in vivo but which, nevertheless, can be incorporated into the peptide structures described herein. Preferred synthetic amino acids are the d-α-amino acids of naturally occurring 1-α-amino acid, mentioned above, as well as non-naturally occurring d- and 1-α-amino acids represented by the formula H2NCHR5COOH where R5 is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5) -alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —C(O)R2 where R2 is selected from the group consisting of hydrogen, hydroxy, lower alkyl, lower alkoxy, and —NR3R4 where R3 and R4 are independently selected from the group consisting of hydrogen and lower alkyl, (g) —S(O)nR6 where n is an integer from 1 to 2 and R6 is lower alkyl and with the proviso that R5 does not define a side chain of a naturally occurring amino acid. Other preferred synthetic amino acids include amino acids wherein the amino group is separated from the carboxyl group by more than one carbon atom such as β-alanine, γ-aminobutyric acid, and the like.

It will also be recognized by those of skill upon reviewing these results that the compositions (e.g., polypeptides and mimetics) described supra can be used to identify telomerase association and activity inhibitors other than the disclosed polypeptide and mimetics. These compositions may be used, for example, in rational drug design for e.g., computer modeling of telomerase activity modulators (e.g., modulators that inhibit the association of TRT and TR or that catalyze the disassociation of the telomerase complex), as positive controls in screens for modulators of telomerase activity, or in competition assays with candidate telomerase activity modulators.

b) Methods

1) Mutagenesis

Mutagenesis of the hTRT coding sequence of pGRN125 was carried out using the methods described by Perez et al., 1994, *J. Biol. Chem.* 269:22485–87. Most of the deletion mutants were generated from the plasmid pGRN125 (Weinrich et al., 1997, supra). Deletion mutants pGRN235 and pGRN236 were made in a secondary round of mutagenesis in an altered pGRN234. pGRN234 was generated by mutating (deleting) the Nco I site in pGRN125 (changing CAC to CAT in the histidine residue at position 754) and introducing a new NcoI site at the translation start site (ATG). Table 2 shows exemplary oligonucleotides used to generate the plasmids expressing the deletion variants of the invention.

TABLE 2

| Oligo Name | Oligo sequence 5'-3' | length | Description |
|---|---|---|---|
| RT1 | GAAGGCCGCCCACGGGCACGTCCGC | 25 | Mutagenesis oligo to delete Nco 1 site from pGRNI25 |
| RT2 | CCCGGCCACCCCAGCCATGGCGCGC GCTCCCC | 32 | Mutagenesis oligo to create Nco 1 site @ATG of pGRN 125 |

TABLE 2-continued

| Oligo Name | Oligo sequence 5'-3' | length | Description |
|---|---|---|---|
| RT5 | TACGGGGTGCTCCTCAAGACGCACTG CCCGCTGCTCCGCCAGCACAGCAGC CCCTGGCAG | 60 | Mutagenesis oligo to create a deletion of aa 415–450 in pGRN125 |
| RT10 | TACTCCATCCTGAAAGCCAAGAACGC AGGGCTGTGCCACCAAGCATTCCTGC TCAAGCTG | 60 | Mutagenesis oligo to create a deletion of aa 1055–1071 in pGRN125 |
| RT11 | CTGTGCCACCAAGCATTCCTGCTCAA GCTGGCCGCAGCCAACCCGGCACTG CCCTCAGAC | 60 | Mutagenesis oligo to create a deletion of aa 1083–1116 in pGRN125. Oligo creates a NheI site. |
| RT3A | ACTCAGGCCCGGCCCCCGCCACACG CTAGCGAGACCAAGCACTTCCTCTAC TCCTCAGGC | 60 | Mutagenesis oligo to create a deletion of aa 192–323 in pGRN125. Oligo creates a NheI site. |
| RT4A | ACTCAGGCCCGGCCCCCGCCACACG CTAGCGTGGTGTCACCTGCCAGACCC GCCGAAGAA | 60 | Mutagenesis oligo to create a deletion of aa 192–271 in pGRN125. Oligo creates a NheI site. |
| RT6A | ATCCCCAAGCCTGACGGGCTGCGGC CGATTGTTAACATGCTGTTCAGCGTG CTCAACTACGAGCGGGCG | 69 | Mutagenesis oligo to create a deletion of aa 638–660 in pGRN125. Oligo creates a Hpa I site. |
| RT8A | ACGTACTGCGTGCGTCGGTATGCCGT GGTCACAGATCTCCAGCCGTACATGC GACAGTTCGTG | 63 | Mutagenesis oligo to create a deletion of aa 748–766 in pGRN125. Oligo creates a BgI II site. |
| RT3A/5 | ACTCAGGCCCGGCCCCCGCCACACG CTAGCCTGCTCCGCCAGCACAGCAG CCCCTGGCAG | 60 | Mutagenesis oligo to create a deletion of aa 192–450 in pGRN125. Oligo creates a NheI site. |
| LM121-WG | GTTCAGATGCCGGCCCACGGCCTATT CCCTCTAGATACCCGGACCCTGGAGG TGCAGAGCGAC | 63 | Mutagenesis oligo to delete aa 930–934. Oligo introduces a new XbaI site |
| LM122-Nuc | CCCTGGGCCTGCCAGCCCCGGGTGC CGGCGCTGCCCCTGAGCCGGAGCGG | 50 | Mutagenesis oligo to delete aa 222–240. Oligo introduces a new Nae I site |
| RT3 | GCTAGTGGACCCCGAAGGCGTCTGG GATGCGAGACCAAGCACTTCCTCTAC TCCTCAGGC | 60 | Mutagenesis oligo to create a deletion of aa200–323 in pGRN125 |
| RT4 | GCTAGTGGACCCCGAAGGCGTCTGG GATGCGTGGTGTCACCTGCCAGACCC GCCGAAGAA | 60 | Mutagenesis oligo to create a deletion of aa 200–271 in pGRN125 |
| RT6 | GACGGGCTGCGGCCGATTGTGAACA TGGACCTGTTCAGCGTGCTCAACTAC GAGCGGGCG | 60 | Mutagenesis oligo to create a deletion of aa 638–660 in pGRN125 |
| RT8 | ACGTACTGCGTGCGTCGGTATGCCGT GGTCACCTTGACAGACCTCCAGCCGT ACATGCGA | 60 | Mutagenesis oligo to create a deletion of aa 748–764 in pGRN125 |

V. Definitions

The following terms are defined infra to provide additional guidance to one of skill in the practice of the invention:

As used herein, a polypeptide region in a first polypeptide "corresponds" to a region in a second polypeptide when the amino acid sequences of the two regions, or flanking the two regions, are the same or substantially identical. Sequences can be aligned by inspection (e.g., alignment of identical sequences) or by computer implemented alignment of the two sequences. Thus, for example, the residues 192 to 323 of the hTRT polypeptide having the sequence set forth in FIG. 1 "correspond" to residues in the same position in a hTRT polypeptide that differs from the FIG. 1 sequence due to polymorphic variation, or other mutations or deletions (e.g., when the two polypeptides are optimally aligned). Alignments may also be carried out using the GAP computer program, version 6.0 (Devereux et al, 1984, *Nucl. Acid. Res.* 12:387; available from the University of Wisconsin Genetics Computer Group, Madison, Wis.). The GAP program utilizes the alignment method of Needleham and Wunsch, 1970 *J. Mol. Biol.* 48: 443–453 as revised by Smith and Waterman, 1981, *Adv. Appl. Math* 2:482. The preferred default parameters for the GAP program include (1) the weighted comparison matrix of Gribskov and Burgess, 1986, *Nuc. Acid. Res.* 14:6745 as described by Schwartz and Dayhoff, eds., 1979, Atlas of Protein Sequence and Structure, National Biomedical Research Foundation, pp. 353–358 (2) a penalty of 3.0 for each gap and an additional 0.10 penalty for each symbol in each gap; and (3) no penalty for end gaps. Alternatively, alignments can be carried out using the BLAST algorithm, which is described in Altschul et al., 1990, *J. Mol. Biol.* 215:403–410 using as defaults a wordlength (W) of 11, the BLOSUM62 scoring matrix (see Henikoff & Henikoff, 1989, *Proc. Natl. Acad. Sci. USA* 89:10915); alignments (B) of 50, expectation (E) of 10, M=5, and N=-4. A modification of BLAST, the "Gapped BLAST" allows gaps to be introduced into the alignments that are returned (Altschul et al., 1997, *Nucleic Acids Res* 1:3389–3402). Software for performing BLAST analyses is publicly available through the National Center for Biotechnology Information (http://www.ncbi.nlm.nih.gov/).

When referring to an "activity" of an hTRT variant, a variant is considered to be active in an assay of it displays at least 40% of the activity characteristic of the hTRT polypeptide having the sequence set forth in FIG. 1 ("wild type"). A variant is considered to lack activity when it has less that 1% of the "wild type" activity. A variant with greater than 1% activity and less than 40% activity has "intermediate activity."

As used herein,"conservative substitution," refers to substitution of amino acids with other amino acids having similar properties (e.g. acidic, basic, positively or negatively charged, polar or non-polar). The following six groups each contain amino acids that are conservative substitutions for one another: 1) alanine (A), serine (S), threonine (T); 2) aspartic acid (D), glutamic acid (E); 3) asparagine (N), glutamine (Q); 4) arginine (R), lysine (K); 5) isoleucine (I), leucine (L), methionine (M), valine (V); and 6) phenylalanine (F), tyrosine (Y), tryptophan (W) (see also, Creighton, 1984, Proteins, W. H. Freeman and Company).

All publications and patent documents cited in this application are incorporated by reference in their entirety and for all purposes to the same extent as if each individual publication or patent document were so individually denoted.

What is claimed is:

1. A polynucleotide encoding a variant of human telomerase reverse transcriptase (hTRT), said variant having processive catalytic activity and comprising a deletion of at least 10 amino acids from region 192–323 or 415–450 of SEQ. ID NO:2.

2. The polynucleotide of claim 1, wherein the variant comprises a deletion of at least 25 amino acids from region 192–323 or 415–450 of SEQ. ID NO:2.

3. The polynucleotide of claim 1, further comprising a promoter sequence operably linked to the nucleotide sequence encoding the hTRT variant.

4. The polynucleotide of claim 1 that has a deletion of at least one region encoding exactly amino acids 192–323, 200–323, 200–271, 222–240, or 415–450 of SEQ. ID NO:2.

5. The polynucleotide of claim 1 that does not comprise a deletion in the region encoding amino acids 415–450.

6. The polynucleotide of claim 5, further comprising a promoter sequence operably linked to the nucleotide sequence encoding the hTRT variant.

7. A method for increasing the proliferative capacity of a human cell in vitro, comprising expressing the polynucleotide of claim 6 in the cell, thereby increasing its proliferative capacity.

8. A method for increasing the proliferative capacity of a human cell in vitro, comprising expressing the polynucleotide of claim 3 in the cell, thereby increasing its proliferative capacity.

9. A method for producing a variant telomerase reverse transcriptase, comprising expressing the polynucleotide of claim 1 in a host cell or in a cell-free expression system.

10. A cell comprising the polynucleotide of claim 1.

11. The cell of claim 10, that is a human cell.

* * * * *

SEQUENCE LISTING

```
<160> NUMBER OF SEQ ID NOS: 21

<210> SEQ ID NO 1
<211> LENGTH: 4015
<212> TYPE: DNA
<213> ORGANISM: Homo sapiens
<220> FEATURE:
<221> NAME/KEY: CDS
<222> LOCATION: (56)..(3454)
<223> OTHER INFORMATION: human telomerase reverse transcriptase
      (hTRT) cDNA

<400> SEQUENCE: 1
gcagcgctgc gtcctgctgc gcacgtggga agccctggcc ccggccaccc ccgcg atg         58
                                                              Met
                                                                1 ccg cgc gct ccc cgc tgc cga gcc gtg cgc tcc ctg ctg cgc agc cac         106
Pro Arg Ala Pro Arg Cys Arg Ala Val Arg Ser Leu Leu Arg Ser His
            5                  10                  15 tac cgc gag gtg ctg ccg ctg gcc acg ttc gtg cgg cgc ctg ggg ccc         154
Tyr Arg Glu Val Leu Pro Leu Ala Thr Phe Val Arg Arg Leu Gly Pro
         20                  25                  30 cag ggc tgg cgg ctg gtg cag cgc ggg gac ccg gcg gct ttc cgc gcg         202
Gln Gly Trp Arg Leu Val Gln Arg Gly Asp Pro Ala Ala Phe Arg Ala
     35                  40                  45 ctg gtg gcc cag tgc ctg gtg tgc gtg ccc tgg gac gca cgg ccg ccc         250
Leu Val Ala Gln Cys Leu Val Cys Val Pro Trp Asp Ala Arg Pro Pro
 50                  55                  60                  65 ccc gcc gcc ccc tcc ttc cgc cag gtg tcc tgc ctg aag gag ctg gtg         298
Pro Ala Ala Pro Ser Phe Arg Gln Val Ser Cys Leu Lys Glu Leu Val
                 70                  75                  80 gcc cga gtg ctg cag agg ctg tgc gag cgc ggc gcg aag aac gtg ctg         346
Ala Arg Val Leu Gln Arg Leu Cys Glu Arg Gly Ala Lys Asn Val Leu
             85                  90                  95 gcc ttc ggc ttc gcg ctg ctg gac ggg gcc cgc ggg ggc ccc ccc gag         394
Ala Phe Gly Phe Ala Leu Leu Asp Gly Ala Arg Gly Gly Pro Pro Glu
        100                 105                 110 gcc ttc acc acc agc gtg cgc agc tac ctg ccc aac acg gtg acc gac         442
Ala Phe Thr Thr Ser Val Arg Ser Tyr Leu Pro Asn Thr Val Thr Asp
    115                 120                 125 gca ctg cgg ggg agc ggg gcg tgg ggg ctg ctg ctg cgc cgc gtg ggc         490
Ala Leu Arg Gly Ser Gly Ala Trp Gly Leu Leu Leu Arg Arg Val Gly
130                 135                 140                 145 gac gac gtg ctg gtt cac ctg ctg gca cgc tgc gcg ctc ttt gtg ctg         538
Asp Asp Val Leu Val His Leu Leu Ala Arg Cys Ala Leu Phe Val Leu
                150                 155                 160 gtg gct ccc agc tgc gcc tac cag gtg tgc ggg ccg ccg ctg tac cag         586
Val Ala Pro Ser Cys Ala Tyr Gln Val Cys Gly Pro Pro Leu Tyr Gln
            165                 170                 175 ctc ggc gct gcc act cag gcc cgg ccc ccg cca cac gct agt gga ccc         634
Leu Gly Ala Ala Thr Gln Ala Arg Pro Pro Pro His Ala Ser Gly Pro
        180                 185                 190 cga agg cgt ctg gga tgc gaa cgg gcc tgg aac cat agc gtc agg gag         682
Arg Arg Arg Leu Gly Cys Glu Arg Ala Trp Asn His Ser Val Arg Glu
    195                 200                 205
```

```
                                                             -continued gcc ggg gtc ccc ctg ggc ctg cca gcc ccg ggt gcg agg agg cgc ggg      730
Ala Gly Val Pro Leu Gly Leu Pro Ala Pro Gly Ala Arg Arg Arg Gly
210             215                 220                 225 ggc agt gcc agc cga agt ctg ccg ttg ccc aag agg ccc agg cgt ggc      778
Gly Ser Ala Ser Arg Ser Leu Pro Leu Pro Lys Arg Pro Arg Arg Gly
                230                 235                 240 gct gcc cct gag ccg gag cgg acg ccc gtt ggg cag ggg tcc tgg gcc      826
Ala Ala Pro Glu Pro Glu Arg Thr Pro Val Gly Gln Gly Ser Trp Ala
            245                 250                 255 cac ccg ggc agg acg cgt gga ccg agt gac cgt ggt ttc tgt gtg gtg      874
His Pro Gly Arg Thr Arg Gly Pro Ser Asp Arg Gly Phe Cys Val Val
        260                 265                 270 tca cct gcc aga ccc gcc gaa gaa gcc acc tct ttg gag ggt gcg ctc      922
Ser Pro Ala Arg Pro Ala Glu Glu Ala Thr Ser Leu Glu Gly Ala Leu
    275                 280                 285 tct ggc acg cgc cac tcc cac cca tcc gtg ggc cgc cag cac cac gcg      970
Ser Gly Thr Arg His Ser His Pro Ser Val Gly Arg Gln His His Ala
290                 295                 300                 305 ggc ccc cca tcc aca tcg cgg cca cca cgt ccc tgg gac acg cct tgt     1018
Gly Pro Pro Ser Thr Ser Arg Pro Pro Arg Pro Trp Asp Thr Pro Cys
                310                 315                 320 ccc ccg gtg tac gcc gag acc aag cac ttc ctc tac tcc tca ggc gac     1066
Pro Pro Val Tyr Ala Glu Thr Lys His Phe Leu Tyr Ser Ser Gly Asp
            325                 330                 335 aag gag cag ctg cgg ccc tcc ttc cta ctc agc tct ctg agg ccc agc     1114
Lys Glu Gln Leu Arg Pro Ser Phe Leu Leu Ser Ser Leu Arg Pro Ser
        340                 345                 350 ctg act ggc gct cgg agg ctc gtg gag acc atc ttt ctg ggt tcc agg     1162
Leu Thr Gly Ala Arg Arg Leu Val Glu Thr Ile Phe Leu Gly Ser Arg
    355                 360                 365 ccc tgg atg cca ggg act ccc cgc agg ttg ccc cgc ctg ccc cag cgc     1210
Pro Trp Met Pro Gly Thr Pro Arg Arg Leu Pro Arg Leu Pro Gln Arg
370                 375                 380                 385 tac tgg caa atg cgg ccc ctg ttt ctg gag ctg ctt ggg aac cac gcg     1258
Tyr Trp Gln Met Arg Pro Leu Phe Leu Glu Leu Leu Gly Asn His Ala
                390                 395                 400 cag tgc ccc tac ggg gtg ctc ctc aag acg cac tgc ccg ctg cga gct     1306
Gln Cys Pro Tyr Gly Val Leu Leu Lys Thr His Cys Pro Leu Arg Ala
            405                 410                 415 gcg gtc acc cca gca gcc ggt gtc tgt gcc cgg gag aag ccc cag ggc     1354
Ala Val Thr Pro Ala Ala Gly Val Cys Ala Arg Glu Lys Pro Gln Gly
        420                 425                 430 tct gtg gcg gcc ccc gag gag gag gac aca gac ccc gtc gcc ctg gtg     1402
Ser Val Ala Ala Pro Glu Glu Glu Asp Thr Asp Pro Arg Arg Leu Val
    435                 440                 445 cag ctg ctc cgc cag cac agc agc ccc tgg cag gtg tac ggc ttc gtg     1450
Gln Leu Leu Arg Gln His Ser Ser Pro Trp Gln Val Tyr Gly Phe Val
450                 455                 460                 465 cgg gcc tgc ctg cgc cgg ctg gtg ccc cca ggc ctc tgg ggc tcc agg     1498
Arg Ala Cys Leu Arg Arg Leu Val Pro Pro Gly Leu Trp Gly Ser Arg
                470                 475                 480 cac aac gaa cgc cgc ttc ctc agg aac acc aag aag ttc atc tcc ctg     1546
His Asn Glu Arg Arg Phe Leu Arg Asn Thr Lys Lys Phe Ile Ser Leu
            485                 490                 495 ggg aag cat gcc aag ctc tcg ctg cag gag ctg acg tgg aag atg agc     1594
Gly Lys His Ala Lys Leu Ser Leu Gln Glu Leu Thr Trp Lys Met Ser
        500                 505                 510 gtg cgg gac tgc gct tgg ctg cgc agg agc cca ggg gtt ggc tgt gtt     1642
Val Arg Asp Cys Ala Trp Leu Arg Arg Ser Pro Gly Val Gly Cys Val
    515                 520                 525
```

-continued

| | |
|---|---|
| ccg gcc gca gag cac cgt ctg cgt gag gag atc ctg gcc aag ttc ctg<br>Pro Ala Ala Glu His Arg Leu Arg Glu Glu Ile Leu Ala Lys Phe Leu<br>530                               535                        540                       545 | 1690 |
| cac tgg ctg atg agt gtg tac gtc gtc gag ctc ctc agg tct ttc ttt<br>His Trp Leu Met Ser Val Tyr Val Val Glu Leu Leu Arg Ser Phe Phe<br>                  550                        555                       560 | 1738 |
| tat gtc acg gag acc acg ttt caa aag aac agg ctc ttt ttc tac cgg<br>Tyr Val Thr Glu Thr Thr Phe Gln Lys Asn Arg Leu Phe Phe Tyr Arg<br>              565                       570                       575 | 1786 |
| aag agt gtc tgg agc aag ttg caa agc att gga atc aga cag cac ttg<br>Lys Ser Val Trp Ser Lys Leu Gln Ser Ile Gly Ile Arg Gln His Leu<br>580                               585                        590 | 1834 |
| aag agg gtg cag ctg cgg gag ctg tcg gaa gca gag gtc agg cag cat<br>Lys Arg Val Gln Leu Arg Glu Leu Ser Glu Ala Glu Val Arg Gln His<br>     595                       600                       605 | 1882 |
| cgg gaa gcc agg ccc gcc ctg ctg acg tcc aga ctc cgc ttc atc ccc<br>Arg Glu Ala Arg Pro Ala Leu Leu Thr Ser Arg Leu Arg Phe Ile Pro<br>610                               615                        620                       625 | 1930 |
| aag cct gac ggg ctg cgg ccg att gtc aac atg gac tac gtc gtg gga<br>Lys Pro Asp Gly Leu Arg Pro Ile Val Asn Met Asp Tyr Val Val Gly<br>              630                       635                       640 | 1978 |
| gcc aga acg ttc cgc aga gaa aag agg gcc gag cgt ctc acc tcg agg<br>Ala Arg Thr Phe Arg Arg Glu Lys Arg Ala Glu Arg Leu Thr Ser Arg<br>                  645                       650                       655 | 2026 |
| gtg aag gca ctg ttc agc gtg ctc aac tac gag cgg gcg cgg cgc ccc<br>Val Lys Ala Leu Phe Ser Val Leu Asn Tyr Glu Arg Ala Arg Arg Pro<br>660                               665                        670 | 2074 |
| ggc ctc ctg ggc gcc tct gtg ctg ggc ctg gac gat atc cac agg gcc<br>Gly Leu Leu Gly Ala Ser Val Leu Gly Leu Asp Asp Ile His Arg Ala<br>     675                       680                       685 | 2122 |
| tgg cgc acc ttc gtg ctg cgt gtg cgg gcc cag gac ccg ccg cct gag<br>Trp Arg Thr Phe Val Leu Arg Val Arg Ala Gln Asp Pro Pro Pro Glu<br>690                               695                        700                       705 | 2170 |
| ctg tac ttt gtc aag gtg gat gtg acg ggc gcg tac gac acc atc ccc<br>Leu Tyr Phe Val Lys Val Asp Val Thr Gly Ala Tyr Asp Thr Ile Pro<br>              710                       715                       720 | 2218 |
| cag gac agg ctc acg gag gtc atc gcc agc atc atc aaa ccc cag aac<br>Gln Asp Arg Leu Thr Glu Val Ile Ala Ser Ile Ile Lys Pro Gln Asn<br>                  725                       730                       735 | 2266 |
| acg tac tgc gtg cgt cgg tat gcc gtg gtc cag aag gcc gcc cat ggg<br>Thr Tyr Cys Val Arg Arg Tyr Ala Val Val Gln Lys Ala Ala His Gly<br>                  740                       745                       750 | 2314 |
| cac gtc cgc aag gcc ttc aag agc cac gtc tct acc ttg aca gac ctc<br>His Val Arg Lys Ala Phe Lys Ser His Val Ser Thr Leu Thr Asp Leu<br>755                               760                        765 | 2362 |
| cag ccg tac atg cga cag ttc gtg gct cac ctg cag gag acc agc ccg<br>Gln Pro Tyr Met Arg Gln Phe Val Ala His Leu Gln Glu Thr Ser Pro<br>770                               775                        780                       785 | 2410 |
| ctg agg gat gcc gtc gtc atc gag cag agc tcc tcc ctg aat gag gcc<br>Leu Arg Asp Ala Val Val Ile Glu Gln Ser Ser Ser Leu Asn Glu Ala<br>              790                       795                       800 | 2458 |
| agc agt ggc ctc ttc gac gtc ttc cta cgc ttc atg tgc cac cac gcc<br>Ser Ser Gly Leu Phe Asp Val Phe Leu Arg Phe Met Cys His His Ala<br>                  805                       810                       815 | 2506 |
| gtg cgc atc agg ggc aag tcc tac gtc cag tgc cag ggg atc ccg cag<br>Val Arg Ile Arg Gly Lys Ser Tyr Val Gln Cys Gln Gly Ile Pro Gln<br>     820                       825                       830 | 2554 |
| ggc tcc atc ctc tcc acg ctg ctc tgc agc ctg tgc tac ggc gac atg<br>Gly Ser Ile Leu Ser Thr Leu Leu Cys Ser Leu Cys Tyr Gly Asp Met<br>     835                       840                       845 | 2602 |

-continued

```
gag aac aag ctg ttt gcg ggg att cgg cgg gac ggg ctg ctc ctg cgt     2650
Glu Asn Lys Leu Phe Ala Gly Ile Arg Arg Asp Gly Leu Leu Leu Arg
850                 855                 860                 865 ttg gtg gat gat ttc ttg ttg gtg aca cct cac ctc acc cac gcg aaa     2698
Leu Val Asp Asp Phe Leu Leu Val Thr Pro His Leu Thr His Ala Lys
                870                 875                 880 acc ttc ctc agg acc ctg gtc cga ggt gtc cct gag tat ggc tgc gtg     2746
Thr Phe Leu Arg Thr Leu Val Arg Gly Val Pro Glu Tyr Gly Cys Val
            885                 890                 895 gtg aac ttg cgg aag aca gtg gtg aac ttc cct gta gaa gac gag gcc     2794
Val Asn Leu Arg Lys Thr Val Val Asn Phe Pro Val Glu Asp Glu Ala
        900                 905                 910 ctg ggt ggc acg gct ttt gtt cag atg ccg gcc cac ggc cta ttc ccc     2842
Leu Gly Gly Thr Ala Phe Val Gln Met Pro Ala His Gly Leu Phe Pro
    915                 920                 925 tgg tgc ggc ctg ctg ctg gat acc cgg acc ctg gag gtg cag agc gac     2890
Trp Cys Gly Leu Leu Leu Asp Thr Arg Thr Leu Glu Val Gln Ser Asp
930                 935                 940                 945 tac tcc agc tat gcc cgg acc tcc atc aga gcc agt ctc acc ttc aac     2938
Tyr Ser Ser Tyr Ala Arg Thr Ser Ile Arg Ala Ser Leu Thr Phe Asn
                950                 955                 960 cgc ggc ttc aag gct ggg agg aac atg cgt cgc aaa ctc ttt ggg gtc     2986
Arg Gly Phe Lys Ala Gly Arg Asn Met Arg Arg Lys Leu Phe Gly Val
            965                 970                 975 ttg cgg ctg aag tgt cac agc ctg ttt ctg gat ttg cag gtg aac agc     3034
Leu Arg Leu Lys Cys His Ser Leu Phe Leu Asp Leu Gln Val Asn Ser
        980                 985                 990 ctc cag acg gtg tgc acc aac atc tac aag atc ctc ctg cag gcg         3082
Leu Gln Thr Val Cys Thr Asn Ile Tyr Lys Ile Leu Leu Leu Gln Ala
    995                 1000                1005 tac agg ttt cac gca tgt gtg ctg cag ctc cca ttt cat cag caa gtt     3130
Tyr Arg Phe His Ala Cys Val Leu Gln Leu Pro Phe His Gln Gln Val
1010                1015                1020                1025 tgg aag aac ccc aca ttt ttc ctg cgc gtc atc tct gac acg gcc tcc     3178
Trp Lys Asn Pro Thr Phe Phe Leu Arg Val Ile Ser Asp Thr Ala Ser
                1030                1035                1040 ctc tgc tac tcc atc ctg aaa gcc aag aac gca ggg atg tcg ctg ggg     3226
Leu Cys Tyr Ser Ile Leu Lys Ala Lys Asn Ala Gly Met Ser Leu Gly
            1045                1050                1055 gcc aag ggc gcc gcc ggc cct ctg ccc tcc gag gcc gtg cag tgg ctg     3274
Ala Lys Gly Ala Ala Gly Pro Leu Pro Ser Glu Ala Val Gln Trp Leu
        1060                1065                1070 tgc cac caa gca ttc ctg ctc aag ctg act cga cac cgt gtc acc tac     3322
Cys His Gln Ala Phe Leu Leu Lys Leu Thr Arg His Arg Val Thr Tyr
    1075                1080                1085 gtg cca ctc ctg ggg tca ctc agg aca gcc cag acg cag ctg agt cgg     3370
Val Pro Leu Leu Gly Ser Leu Arg Thr Ala Gln Thr Gln Leu Ser Arg
1090                1095                1100                1105 aag ctc ccg ggg acg acg ctg act gcc ctg gag gcc gca gcc aac ccg     3418
Lys Leu Pro Gly Thr Thr Leu Thr Ala Leu Glu Ala Ala Ala Asn Pro
                1110                1115                1120 gca ctg ccc tca gac ttc aag acc atc ctg gac tga tggccacccg          3464
Ala Leu Pro Ser Asp Phe Lys Thr Ile Leu Asp
            1125                1130 cccacagcca ggccgagagc agacaccagc agccctgtca cgccgggctc tacgtcccag   3524
ggagggaggg gcggcccaca cccaggcccg caccgctggg agtctgaggc ctgagtgagt   3584
gtttggccga ggcctgcatg tccggctgaa ggctgagtgt ccggctgagg cctgagcgag   3644
tgtccagcca agggctgagt gtccagcaca cctgccgtct tcacttcccc acaggctggc   3704
```

-continued

```
gctcggctcc accccagggc cagcttttcc tcaccaggag cccggcttcc actccccaca    3764
taggaatagt ccatccccag attcgccatt gttcacccct cgccctgccc tcctttgcct    3824 tccacccca ccatccaggt ggagaccctg agaaggaccc tgggagctct gggaatttgg    3884
agtgaccaaa ggtgtgccct gtacacaggc gaggaccctg cacctggatg ggggtccctg    3944
tgggtcaaat tgggggagg tgctgtggga gtaaaatact gaatatatga gtttttcagt     4004
tttgaaaaaa a                                                         4015
```

<210> SEQ ID NO 2
<211> LENGTH: 1132
<212> TYPE: PRT
<213> ORGANISM: Homo sapiens

<400> SEQUENCE: 2

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320
```

-continued

```
Cys Pro Pro Val Tyr Ala Glu Thr Lys His Phe Leu Tyr Ser Ser Gly
            325                 330                 335

Asp Lys Glu Gln Leu Arg Pro Ser Phe Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
    530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
            725                 730                 735
```

-continued

```
Asn Thr Tyr Cys Val Arg Arg Tyr Ala Val Gln Lys Ala Ala His
        740                 745                 750
Gly His Val Arg Lys Ala Phe Lys Ser His Val Ser Thr Leu Thr Asp
            755                 760                 765
Leu Gln Pro Tyr Met Arg Gln Phe Val Ala His Leu Gln Glu Thr Ser
        770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
        835                 840                 845
Met Glu Asn Lys Leu Phe Ala Gly Ile Arg Arg Asp Gly Leu Leu Leu
    850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
Pro Trp Cys Gly Leu Leu Leu Asp Thr Arg Thr Leu Glu Val Gln Ser
    930                 935                 940
Asp Tyr Ser Ser Tyr Ala Arg Thr Ser Ile Arg Ala Ser Leu Thr Phe
945                 950                 955                 960
Asn Arg Gly Phe Lys Ala Gly Arg Asn Met Arg Arg Lys Leu Phe Gly
                965                 970                 975
Val Leu Arg Leu Lys Cys His Ser Leu Phe Leu Asp Leu Gln Val Asn
            980                 985                 990
Ser Leu Gln Thr Val Cys Thr Asn Ile Tyr Lys Ile Leu Leu Leu Gln
        995                 1000                1005
Ala Tyr Arg Phe His Ala Cys Val Leu Gln Leu Pro Phe His Gln Gln
    1010                1015                1020
Val Trp Lys Asn Pro Thr Phe Phe Leu Arg Val Ile Ser Asp Thr Ala
1025                1030                1035                1040
Ser Leu Cys Tyr Ser Ile Leu Lys Ala Lys Asn Ala Gly Met Ser Leu
                1045                1050                1055
Gly Ala Lys Gly Ala Ala Gly Pro Leu Pro Ser Glu Ala Val Gln Trp
            1060                1065                1070
Leu Cys His Gln Ala Phe Leu Leu Lys Leu Thr Arg His Arg Val Thr
        1075                1080                1085
Tyr Val Pro Leu Leu Gly Ser Leu Arg Thr Ala Gln Thr Gln Leu Ser
    1090                1095                1100
Arg Lys Leu Pro Gly Thr Thr Leu Thr Ala Leu Glu Ala Ala Ala Asn
1105                1110                1115                1120
Pro Ala Leu Pro Ser Asp Phe Lys Thr Ile Leu Asp
                1125                1130

<210> SEQ ID NO 3
<211> LENGTH: 6
<212> TYPE: PRT
```

-continued

```
<213> ORGANISM: Homo sapiens
<220> FEATURE:
<221> NAME/KEY: PEPTIDE
<222> LOCATION: (1)..(6)
<223> OTHER INFORMATION: amino acid positions 560-565 from hTRT

<400> SEQUENCE: 3

Phe Phe Tyr Val Thr Glu
  1               5

<210> SEQ ID NO 4
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: amino acid positions 405-418 from hTRT

<400> SEQUENCE: 4

Tyr Gly Val Leu Leu Lys Thr His Cys Pro Leu Arg Ala Ala
  1               5                  10

<210> SEQ ID NO 5
<211> LENGTH: 4
<212> TYPE: PRT
<213> ORGANISM: Homo sapiens
<220> FEATURE:
<221> NAME/KEY: PEPTIDE
<222> LOCATION: (1)..(4)
<223> OTHER INFORMATION: amino acid positions 561-564 from hTRT

<400> SEQUENCE: 5

Phe Tyr Val Thr
  1

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:RT1 oligo

<400> SEQUENCE: 6
gaaggccgcc cacgggcacg tccgc                                       25

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:RT2 oligo

<400> SEQUENCE: 7
cccggccacc ccagccatgg cgcgcgctcc cc                               32

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence:RT5 oligo

<400> SEQUENCE: 8
tacggggtgc tcctcaagac gcactgcccg ctgctccgcc agcacagcag cccctggcag   60
```

```
<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence:RT10 oligo

<400> SEQUENCE: 9
tactccatcc tgaaagccaa gaacgcaggg ctgtgccacc aagcattcct gctcaagctg      60

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:RT11 oligo

<400> SEQUENCE: 10
ctgtgccacc aagcattcct gctcaagctg gccgcagcca acccggcact gccctcagac      60

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence:RT3A oligo

<400> SEQUENCE: 11
actcaggccc ggcccccgcc acacgctagc gagaccaagc acttcctcta ctcctcaggc      60

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence:RT4A oligo

<400> SEQUENCE: 12
actcaggccc ggcccccgcc acacgctagc gtggtgtcac ctgccagacc cgccgaagaa      60

<210> SEQ ID NO 13
<211> LENGTH: 69
<212> TYPE: DNA
<213> ORGANISM: Artificial Sequence
<220> FEATURE:
<223> OTHER INFORMATION: Description of Artificial Sequence:RT6A oligo

<400> SEQUENCE: 13
atccccaagc ctgacgggct gcggccgatt gttaacatgc tgttcagcgt gctcaactac      60
gagcgggcg                                                             69

<210> SEQ ID NO 14
<211> LENGTH: 63
<212> TYPE: DNA
<213> ORGANISM: Artificial Sequence
<220> FEATURE:
<223> OTHER INFORMATION: Description of Artificial Sequence:RT8A oligo

<400> SEQUENCE: 14
acgtactgcg tgcgtcggta tgccgtggtc acagatctcc agccgtacat gcgacagttc      60
gtg                                                                   63

<210> SEQ ID NO 15
<211> LENGTH: 60
<212> TYPE: DNA
```

```
<213> ORGANISM: Artificial Sequence
<220> FEATURE:
<223> OTHER INFORMATION: Description of Artificial Sequence:RT3A/5 oligo

<400> SEQUENCE: 15
actcaggccc ggcccccgcc acacgctagc ctgctccgcc agcacagcag cccctggcag      60

<210> SEQ ID NO 16
<211> LENGTH: 63
<212> TYPE: DNA
<213> ORGANISM: Artificial Sequence
<220> FEATURE:
<223> OTHER INFORMATION: Description of Artificial Sequence:LM121-WG
      oligo

<400> SEQUENCE: 16
gttcagatgc cggcccacgg cctattccct ctagataccc ggaccctgga ggtgcagagc      60
gac                                                                   63

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence:LM122-Nuc
      oligo

<400> SEQUENCE: 17
ccctgggcct gccagccccg ggtgccggcg ctgccnctga gccggagcgg               50

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence:RT3 oligo

<400> SEQUENCE: 18
gctagtggac cccgaaggcg tctgggatgc gagaccaagc acttcctcta ctcctcaggc     60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence:RT4 oligo

<400> SEQUENCE: 19
gctagtggac cccgaaggcg tctgggatgc gtggtgtcac ctgccagacc cgccgaagaa     60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence:RT6 oligo

<400> SEQUENCE: 20
gacgggctgc ggccgattgt gaacatggac ctgttcagcg tgctcaacta cgagcgggcg     60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence:RT8 oligo
```

```
<400> SEQUENCE: 21
acgtactgcg tgcgtcggta tgccgtggtc accttgacag acctccagcc gtacatgcga        60
```